United States Patent [19]
Yokoyama et al.

[11] Patent Number: 5,729,342
[45] Date of Patent: Mar. 17, 1998

[54] METHOD OF ANALYZING THE CONCENTRATION OF COMPONENTS IN A SOLUTION

[75] Inventors: Issei Yokoyama; Masaru Inoue, both of Miyanohigashi-machi, Japan

[73] Assignee: Horiba, Ltd., Kyoto, Japan

[21] Appl. No.: 787,648

[22] Filed: Jan. 23, 1997

[30] Foreign Application Priority Data

Jan. 24, 1996 [JP] Japan ................... 8-029951

[51] Int. Cl.⁶ ................... G01N 21/59; G01N 21/90
[52] U.S. Cl. ................... 356/319; 356/326; 356/436
[58] Field of Search ................... 356/326, 319, 356/436

[56] References Cited

U.S. PATENT DOCUMENTS 5,272,345 12/1993 Durham et al. ................... 356/436 X

*Primary Examiner*—Vincent P. McGraw
*Attorney, Agent, or Firm*—Price, Gess & Ubell

[57] ABSTRACT

A method of analyzing the concentration of components in a fluid solution that can be contaminated with gas bubbles includes applying a spectrum of light to a test cell holding a sample fluid solution and detecting the measurement of the intensity of light passing through the test cell. A gas of the type that would be found in the sample fluid solution can be initially inserted into the test cell with light of a predetermined range of wavelengths scanning the test cell to obtain a reference spectrum. The test cell is then filled with the sample fluid solution and the light measurement is again conducted to obtain a sample spectrum. Data processing can occur to derive a light absorbance spectrum from the reference spectrum and sample spectrum to enable a determination of the percentage of concentrations of each component from the light absorbance spectrum, including the percentage of gas. Adding the determined percentages of concentration will provide a total amount, and comparing this total amount with a predetermined value can verify the accuracy of the concentration of components. If the data is contaminated as a result of an excess presence of gas bubbles, this data can be discarded to insure that the proper amount of concentrations is determined.

10 Claims, 4 Drawing Sheets

METHOD OF ANALYZING THE CONCENTRATION OF COMPONENTS IN A SOLUTION

BACKGROUND OF THE INVENTION

1. Field of the Invention

The present invention relates to a method of analyzing concentrations of a plurality of components contained in a solution and, more particularly, a method of assuring the accuracy of fluid concentrations that may contain gas bubbles.

2. Description of Related Art

The prior art has frequently sought to determine the concentrations of a plurality of components contained in a solution. One form of a concentration analysis is an optical approach, whereby light fore a light source will be transmitted through a sample solution and also through a reference sample of a known concentration. The resulting sample spectrum and reference spectrum will be used to obtain an absorbance or absorption spectrum, and this absorbance or absorption spectrum will be subject to data processing, such as a multi-variation analysis procedure.

Referring to FIG. 2A, a solvent $B_o$ is deposited in a test cell 1 and is used as the reference sample. The cell 1 is positioned in the optical path between a spectroscopic apparatus 2 and a detector 3. Light, for example monochromatic light from a light source 4, is directed to the spectroscopic apparatus, such as a spectroscope and then scanning is made with the light of a wavelength $\lambda$ through the test cell 1. The light transmitted through the test cell is received by a detector 3 to obtain a reference spectrum $I_0(\lambda)$. Referring to FIG. 2B, the solution S is disclosed as the sample which is positioned within the cell 1. Solution S will comprise the solvent $B_0$ plus components $B_1, B_2 \ldots B_n$. The cell 1 is again positioned between the spectroscopic apparatus 2 and the detector 3 with monochromatic light coming from a light source 4. The spectroscope divides the light and provides a scanning of the cell 1 with light of various wavelengths $\lambda$. The light that is transmitted through the cell 1 is received by the detector 3 to obtain a sample spectrum $I(\lambda)$.

The respective reference spectra and sample spectra are then used to obtain a light absorbance or absorption spectrum $A(\lambda)$ by the following equation:

$$A(\lambda)=\log_{10}[I_0(\lambda)/I(\lambda)] \tag{1}$$

The absorbance or absorption spectrum $A(\lambda)$ is then subjected to data processing by a known data processing method, such as a multi-variation analysis method. As a result of this data processing, the concentrations of the above components $B_1, B_2, \ldots B_n$ can then be obtained. Problems have occurred, however, with this conventional method of a concentration analysis method, when a solvent $B_o$ is used as a reference material. The concentration of the solvent $B_o$ itself cannot be computed. In addition, if there are gas bubbles contained in the sample solution S, the light transmissivity of the solution S becomes generally high and accordingly, the sample spectrum $I(\lambda)$ becomes larger than in the case where there are no bubbles in the solution S.

Referring to FIG. 3, the absorbance or absorption spectrum $A(\lambda)$ is smaller in the case where the bubbles are contained in the solution S, as shown in graph element a, when compared with a solution that is free of any bubbles, as shown in the graph element b. For this reason, the concentrations of the components $B_1, B_2, \ldots B_n$ will become smaller than the actual amounts in the sample with a resulting error. In addition, in the conventional concentration analysis method, the concentration of the solvent $B_o$ is unknown and therefore it is not possible to judge accurately whether bubbles are contained in the solution S or not, and accordingly it has not been possible to remove the effect of bubbles during a data processing procedure.

OBJECTS AND SUMMARY OF THE INVENTION

The present invention provides a concentration analysis method that permits an accurate measurement of components contained in a sample solution by lowering the concentration errors caused by gas bubbles. The present invention directs an appropriate range of wavelengths of light so that it is transmitted through a sample solution and a reference sample to obtain a sample spectrum and a reference spectrum. An absorbance or absorption spectrum is then derived from the spectra. The absorbance or absorption spectrum is subject to data processing. The concentration analysis is carried out by using a gas having the same component as the air or gas bubble in the reference sample. That is, if the reference sample is prone to have a particular type of gas, that gas can be used in the reference sample so that, when the total value of the concentrations of the components contained in the solution is determined to be outside a prescribed range, it can be determined that bubbles are contained in the sample solution with resulting errors. Accordingly, a method of analyzing the concentrations of components in a fluid solution with a source of light, a test cell for holding the fluid solution, and a detector for measuring the intensity of light passing through the test cell is provided. A computer with an appropriate algorithm program can be used for data processing the measured intensity of light.

The steps of the present invention include inserting into the test cell a gas of a type that would be found in the fluid solution and then directing light of a predetermined wavelength through the test cell with the gas to the detector to obtain a reference spectrum. A sample fluid solution can be then inserted into the test cell and again light is directed of the same predetermined wavelength through the test cell to obtain a sample spectrum. A light absorbance or absorption spectrum can be derived from the respective reference spectrum and sample spectrum and then the light absorbance spectrum can be appropriately processed to determine the percentage of concentrations of each component in the sample fluid solution. The determined percentages of concentration can then be added to provide a total amount, and this total amount can then be compared with a predetermined value to verify the accuracy of the concentration of the components. For example, it can be assumed that an ideal condition with no bubbles in the sample fluid solution will permit the relative percentages of concentrations to add up to a 100% total. A predetermined value of, for example, 99%, can be utilized to verify the accuracy of the method of analyzing the concentrations.

Alternatively, a correction coefficient, for example, of 100 divided by the total amount of determined percentages can be utilized to multiply the total amount of a specific concentration of a component to correct for the existence of bubbles in the sample fluid solution.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a method of analyzing the concentration of components in a solution.

The present invention provides a novel method of processing a reference spectrum and a sample spectrum to determine the existence of a contaminant, such as gas bubbles, in the sample solution, and when such a contaminant is discovered, the data can either be rejected or a correction coefficient can be applied to adjust the value of the concentrations of the components contained in the solution. In the method of the present invention, light from a light source of a predetermined range of wavelengths can be directed to a test cell containing a gas of the type that would be found in the sample fluid solution. The light transmitted through the test cell can be detected to obtain a reference spectrum.

A sample fluid solution can be inserted into the test cell and again light can be directed of the predetermined range of wavelengths through the test cell to obtain a sample spectrum. Utilizing the respective reference spectrum and the sample spectrum, a light absorption or absorbance spectrum can be derived. Based on the light absorbance or absorption spectrum, it is possible to determine the percentage of concentration of each component through the use of data processing such as a multi-variation analysis method. As a result of this data processing, the individual concentrations by percentages corresponding to the sample fluid solution is determined. An example of a calibration matrix that can be obtained by a multi-variation analysis as follows:

$$\begin{vmatrix} C_0 \\ C_1 \\ C_2 \\ \cdot \\ \cdot \\ \cdot \\ C_n \end{vmatrix} \begin{vmatrix} M_{0,0} & M_{0,1} & M_{0,2} & \ldots & M_{0,m} \\ M_{1,0} & M_{1,1} & M_{1,2} & \ldots & M_{1,m} \\ \cdot & & & & \\ \cdot & & & & \\ \cdot & & & & \\ M_{n,0} & M_{n,1} & M_{n,2} & \ldots & M_{n,m} \end{vmatrix} \begin{vmatrix} A(\lambda_0) \\ A(\lambda_1) \\ A(\lambda_2) \\ \cdot \\ \cdot \\ \cdot \\ A(\lambda_m) \end{vmatrix}$$

Concentration    Calibration Matrix    Absorbance Spectrum

Figure 1A:
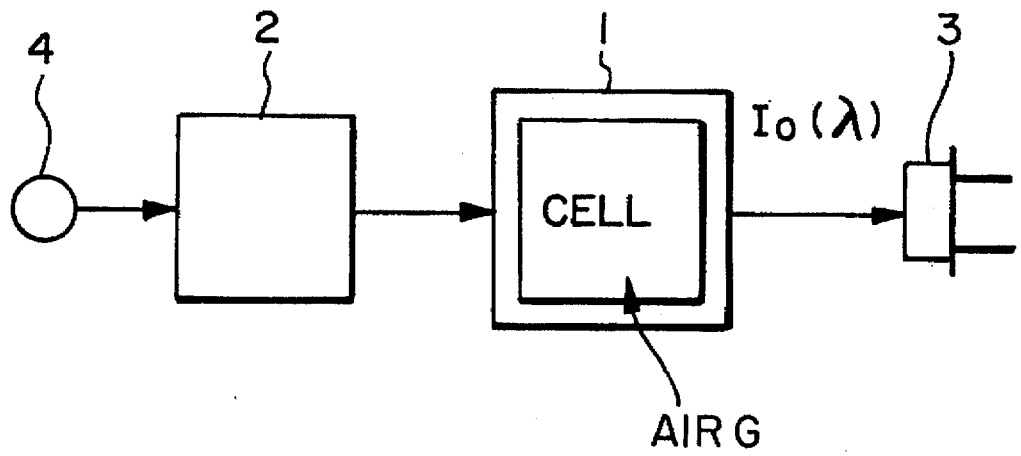
FIGS. 1A and 1B are schematic views to illustrate the apparatus for practicing the concentration analysis method of the present invention.
Figure 1B:
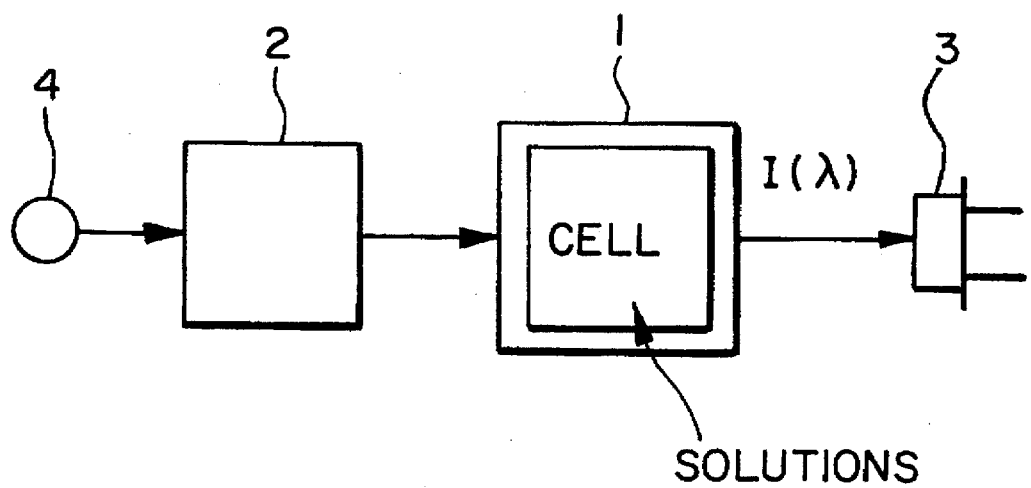
Figure 2A:
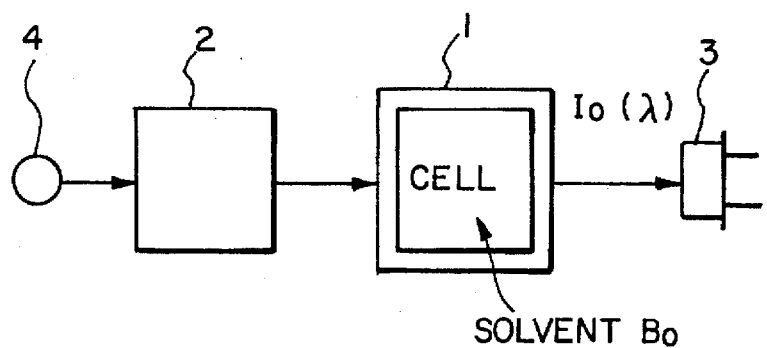
FIGS. 2A and 2B are views disclosing the conventional apparatus for practicing the concentration analysis method.
Figure 2B:
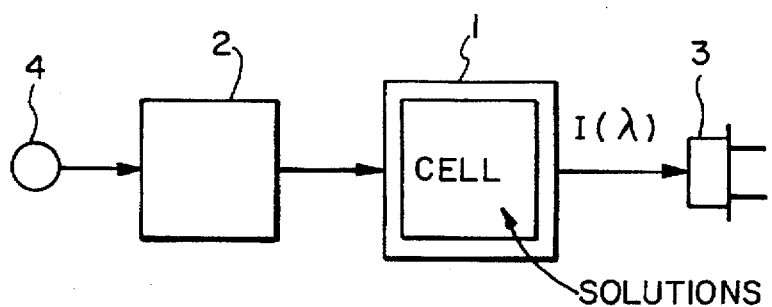
Figure 3:
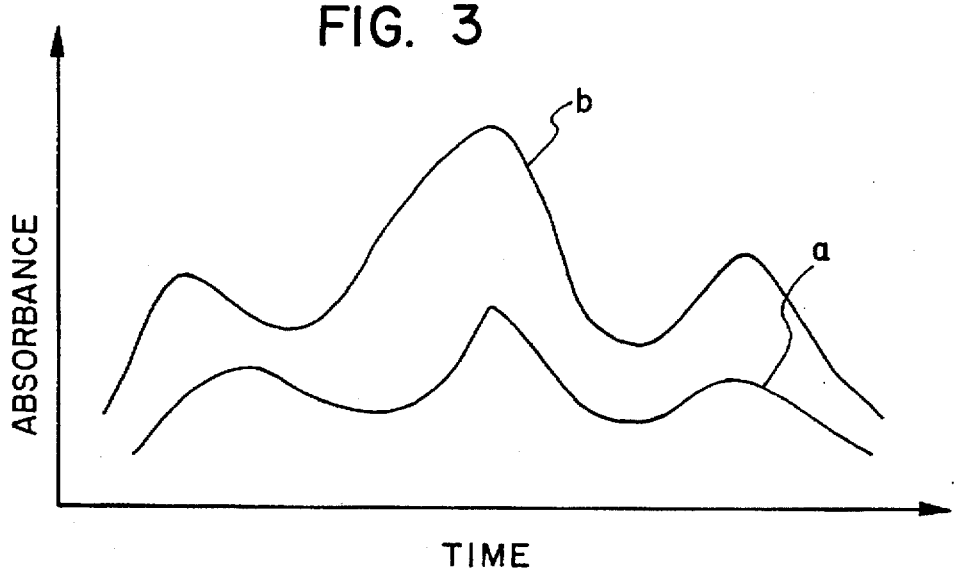
FIG. 3 is an absorbance or absorption spectrum graph disclosing a comparison with a solution containing bubbles and a solution not containing bubbles.

Referring to FIG. 1A and FIG. 1B, schematic views of apparatus utilized in a first embodiment of the concentration analysis of the present invention is disclosed. A known light source 4 is utilized with a spectroscopic means 2, such as a spectroscope, to provide a scanning light beam of a predetermined range of wavelengths $\lambda$. This light can then be transmitted through a test cell 1 to be received by a detector 3 to obtain a measurement of the transmitted light. As is known in this field, the information contained in this transmitted light can be processed to determine characteristics associated with the presence of components in a test solution. In FIG. 1A, a gas, G, such as would be expected to be found in the solution sample, is sealed into the cell 1. For example, air is disclosed in FIG. 1A. Alternatively, other forms of gas, such as nitrogen, etc., could be used if it would be expected that gas bubbles of that form of gas could be found in the sample solution. The cell 1 with the air sealed therein is provided in the light path between the spectroscopic means 2 and the detector 3. Monochromatic light from the light source 4 is spectroscopically divided by the spectroscopic means 2 and then scanned into the test cell 1. For example, light of each wavelength $\lambda$ is then transmitted through the cell to be received by the detector 3 to obtain a reference spectrum $I_o(\lambda)$.

Referring to FIG. 1B, the above procedure is repeated with the sample solution S placed into the cell and again monochromatic light from the light source 4 is spectroscopically divided by the spectroscopic means 2 and scanned with light of each wavelength $\lambda$. The light transmitted through the sample cell is received by the detector 3 to obtain a sample spectrum $I(\lambda)$. Using the respective reference spectrum and sample spectrum, a light absorbance spectrum $A(\lambda)$ can be obtained, as is known in this field. The absorbance spectrum $A(\lambda)$ is then subject to a data processing, for example, in a CPU system, with an algorithm of a known multi-variation analysis method. As a result of this data processing, there can be obtained the concentrations $C_0, C_1, C_2, \ldots C_n$ corresponding to the solvent $B_0$, components $B_1, B_2, \ldots B_n$, respectively. It has been found that the total amount T of the concentrations $C_0, C_1, C_2, \ldots C_n$ is usually $T=C_0+C_1+C_2+ \ldots +C_n \approx 100\%$.

However, in those cases where bubbles are contained in the sample solution S, an error occurs in that the amount of concentration appears to be smaller than in the case where no bubbles would be contained in the sample solution S. That is, the above total concentration T becomes smaller than 100%. As a result, the measurement of the total amount T of the concentration of the components $B_1, B_2, \ldots B_N$ containing the solvent $B_o$ in the sample solution S becomes an index to signify the presence or absence of bubbles in the solution S and whether there is a large or small amount of bubbles.

Accordingly, when the above total amount T is more than a certain level, for example, more than 99%, it can be judged that no bubbles are contained in the solution, and when the amount T is less than 99%, it is deemed that bubbles are contained and the data then has the effects of the bubbles, and such a data should be excluded. For example, in case a concentration is computed by subjecting the data at the five points to a moving average method and there is one group of data which has been judged to be under the effect of bubbles, then an averaging of the data of the four points remaining should be taken after excluding the erroneous data. By this method, there can be obtained an accurate concentration value subject to only a small effect from bubbles.

Figure 4:
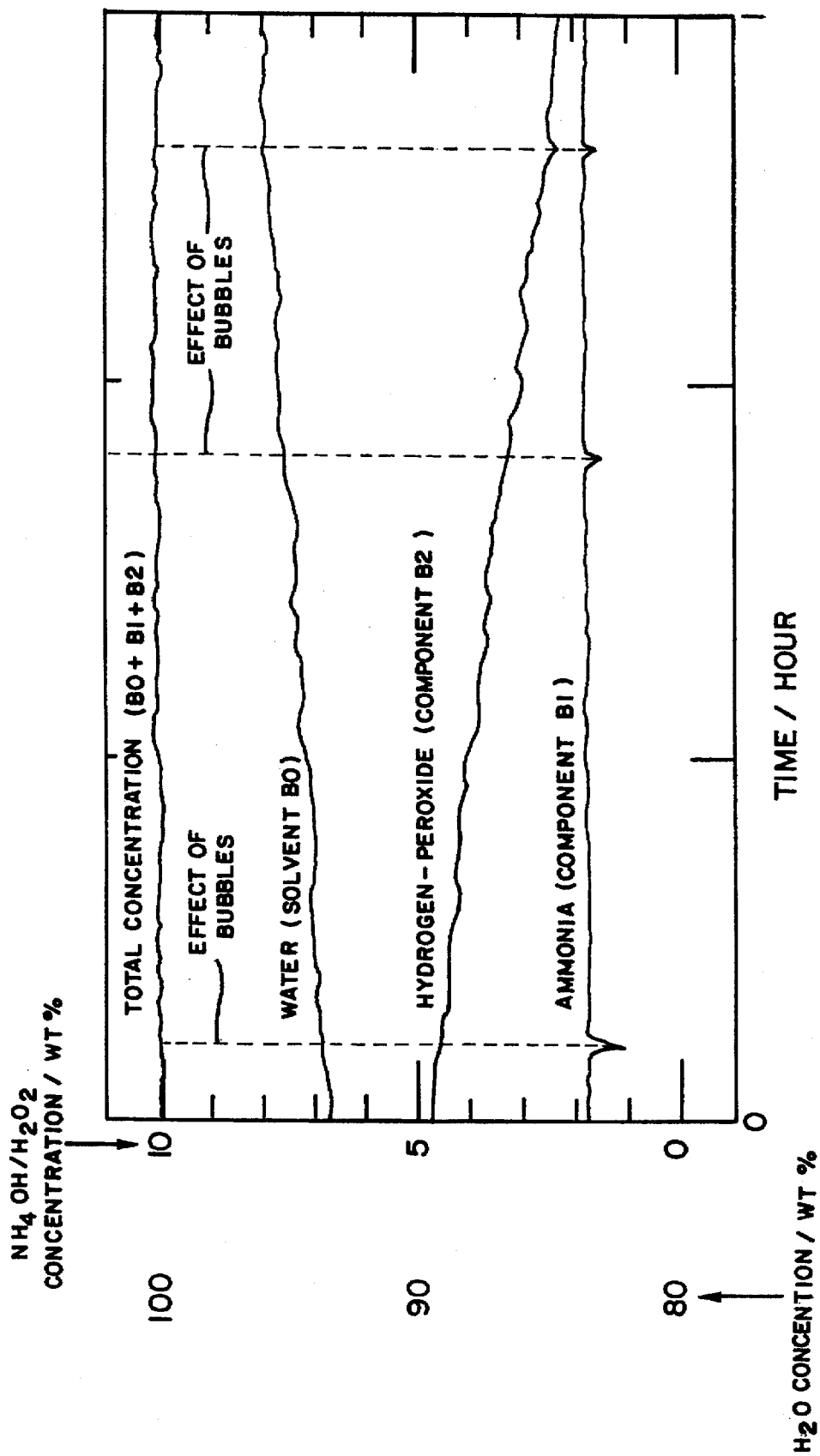
FIG. 4 is a graph of concentrations of a water solution of ammonia and hydrogen peroxide with oxygen gas.
Figure 5:
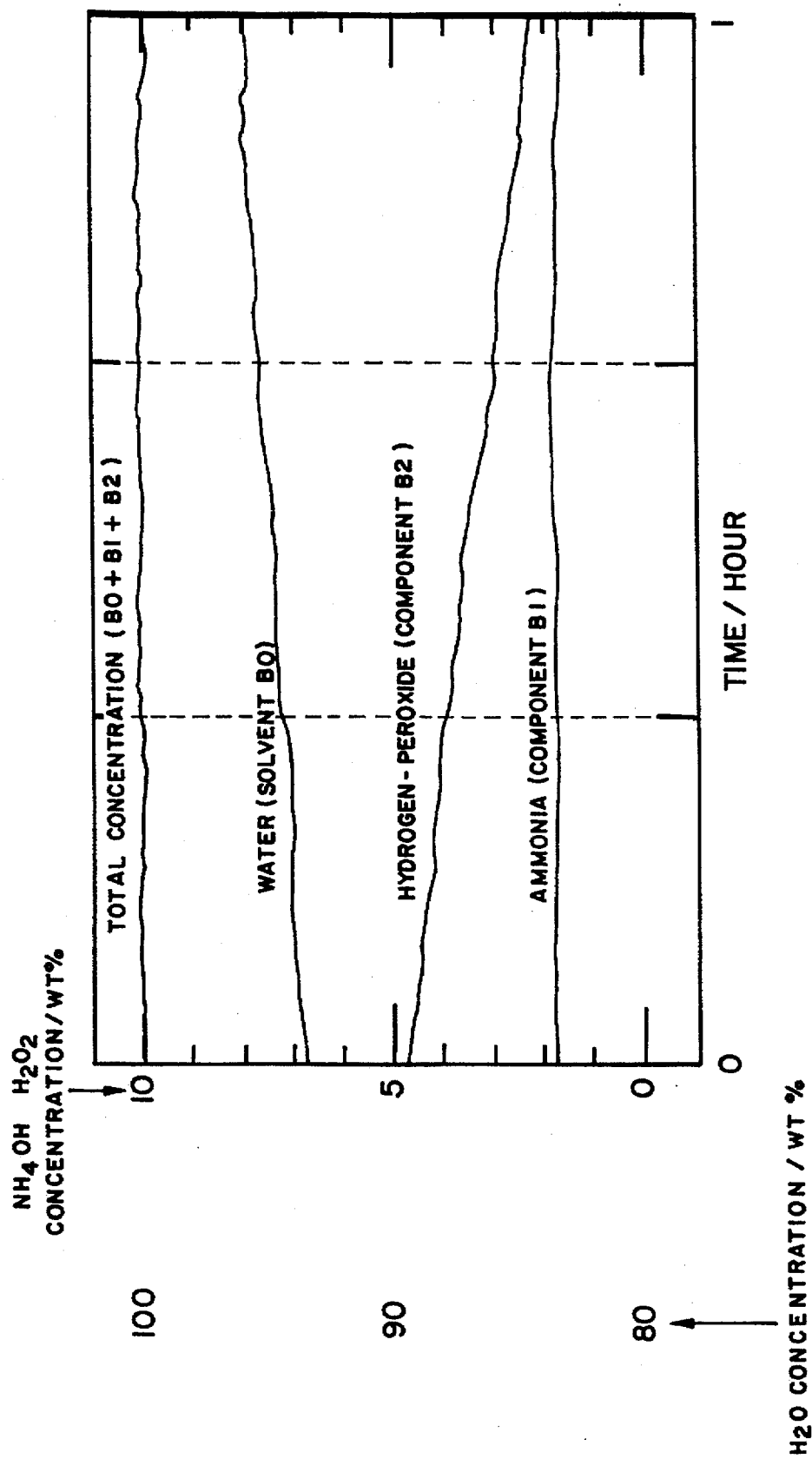
FIG. 5 is a graph of the concentrations of FIG. 4 with the effects of oxygen gas removed.

An illustrative example of an application of the present invention can be seen in FIGS. 4 and 5. In the semiconductor industry wafers are cleaned by a solution of water, ammonia and hydrogen peroxide and there is a desire to maintain the consistency of these components. Such a cleaning solution will have numerous bubbles of oxygen because hydrogen peroxide can break down to water and oxygen gas. Thus, the effects of oxygen bubbles must be taken into account. FIG. 4 discloses a plot of concentrations wherein the hydrogen peroxide is dissolving in the cleaning solution over a period of time with the generation of oxygen bubbles. The data plotted in FIG. 4 has the effect of bubbles, as can be seen by the variations in the data purportedly representing the concentration of ammonia.

FIG. 5 discloses a plot of sampling data used in FIG. 4 after the data is subject to a five point average method with one group of data being judged as under the adverse effect of bubbles in accordance with the present invention, and this contaminated data is discarded with an averaging of the remaining data with the four remaining points of data plotted in FIG. 5.

The concentration analysis method in the first embodiment as described above can be applied even if the bubbles generate or extinguish or then- amount varies during the measurement of the sample spectrum I ($\lambda$), but when such variation does not occur, a practice may be made as in a second embodiment of the invention as follows.

In this embodiment, the steps to the stage that the sample spectrum I ($\lambda$) is obtained, and based on it the concentrations of the solvent $B_o$ and components $B_1$, $B_2$, . . . $B_n$ are obtained, are the same as those of the first embodiments. The different points are explained below.

When bubbles are contained in the sample solution S, the total mount T of the component concentrations becomes smaller than 100%. Now, assuming that the bubbles of k % in volume are contained, T≈(100−k)%. In this case, the concentrations $C_0$, $C_1$, $C_2$, . . . $C_n$ of the solvent $B_o$ and components $B_1$, $B_2$, . . . $B_n$ have become a magnitude of (100−k)/100-fold, i.e., T/100-fold, compared with the case where there is no effect of bubbles. The term fold being the value of multiplying the total amount of concentration by 100 divided by the total mount of determined percentages.

Accordingly, the concentrations $C_0$, $C_1$, $C_2$, . . . $C_n$ obtained by the above data processing procedure are multiplied by an inverse number of the above T/100, namely, 100/T, as a correction coefficient so that there can be obtained the sample concentrations after eliminating the effects of the bubbles $C_0'$, $C_1'$, $C_2'$, . . . $C_n'$. Namely, the conditions are made to be the following:

$C_i' = C_i \times 100/T$, where $i=0, 1, 2, \ldots n$.

In either of the above embodiments, an air G is used as a reference sample, but instead of the air G, a gas having the same component as the bubble in the solution S may be used.

This invention is practiced in the embodiments as described above, and shows the following effects. According to this invention, the concentration of the solvent contained in the solution is known, so that the total amount of the concentrations of solvent and components can be exactly obtained. And, depending on the state whether the above total amount is in a certain predetermined range or not, identification is possible to find whether bubbles are contained in the solution or not. Accordingly, when bubbles are contained in the solution, such measurements are excluded and only acceptable values are averaged to obtain a concentration, or alternatively, the resulting concentration may be multiplied by an optional correction coefficient to obtain an accurate concentration of the components contained in the solution.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method of analyzing the concentrations of components in a fluid solution with a source of light, a test cell for holding a sample fluid solution, a detector for measuring the intensity of light passing through the test cell and means for data processing the measured intensity of light, comprising the steps of:

inserting into the test cell a gas of the type that would be found in the sample fluid solution;

directing light of a predetermined range of wavelengths through the test cell with the gas to the detector to obtain a reference spectrum;

inserting into the test cell the sample fluid solution;

directing light of the predetermined range of wavelengths through the test cell with the fluid solution to obtain a sample spectrum;

deriving a light absorbance spectrum from the reference spectrum and the sample spectrum;

determining the percentage of concentrations of each component from the light absorbance spectrum;

adding the determined percentages of concentration to provide a total amount; and comparing the total amount with a predetermined value to verify the accuracy of the concentration of components.

2. The method of claim 1, wherein the gas is air.

3. The method of claim 1, wherein the predetermined value is 99%.

4. The method of claim 1 further including the steps of repeating the measurements of the sample fluid solution for a plurality of times and only using the determined percentages of concentration whose total amount is greater than the predetermined value and averaging those concentrations greater than the predetermined value to provide a final concentration.

5. The method of claim 1 further including multiplying the total amount of concentration by a correction coefficient of 100 divided by the total amount of determined percentages.

6. A method of determining the presence of gas bubbles in a sample liquid solution and their impact on analyzing the concentration of components in a solution contained in a test cell with a spectrum of light; a detector measures the intensity of light passing through the test cell and the collected data is processed, comprising the steps of:

inserting into the test cell a gas of the type that would be found in the sample fluid solution;

directing light of a predetermined range of wavelength through the test cell with the gas to the detector to obtain a reference spectrum of data;

inserting into the test cell the sample fluid solution;

directing light of the predetermined range of wavelengths through the test cell with the fluid solution to obtain a sample spectrum of data;

deriving a light absorbance spectrum from the reference spectrum and the sample spectrum;

determining the percentage of concentrations of each component from the light absorbance spectrum, including the percentage of gas;

adding the determined percentages of concentration to provide a total amount;

comparing the total amount with a predetermined value to verify the accuracy of the concentration of components; and indicating if a portion of the sample spectrum of data has been affected by gas bubbles.

7. The method of claim 6, wherein the gas is air.

8. The method of claim 6, wherein the predetermined value is 99%.

9. The method of claim 6 further including the steps of repeating the measurements of the sample fluid solution for a plurality of times and only using the determined percentages of concentration whose total amount is greater than the predetermined value and averaging those concentrations greater than the predetermined value to provide a final concentration free from the effect of gas bubbles.

10. The method of claim 6 further including multiplying the total amount of concentration by a correction coefficient of 100 divided by the total amount of determined percentages.

* * * * *